United States Patent [19]

Kallury et al.

[11] Patent Number: 5,405,766
[45] Date of Patent: Apr. 11, 1995

[54] IMMOBILIZATION OF BIOLOGICALLY ACTIVE PROTEIN ON A SUPPORT WITH A 7-18 CARBON SPACER AND A BIFUNCTIONAL PHOSPHOLIPID

[75] Inventors: Krishna M. R. Kallury, Scarborough; Michael Thompson, Mississauga; William E. Lee, Medicine Hat, all of Canada

[73] Assignee: Her Majesty the Queen in right of Canada, as represented by the Minister of National Defence, Ottawa, Canada

[21] Appl. No.: 36,867

[22] Filed: Mar. 25, 1993

[30] Foreign Application Priority Data

Mar. 26, 1992 [CA] Canada ................................. 2064683

[51] Int. Cl.⁶ ...................... C12N 11/00; C12N 11/06; C12N 11/14; G01N 33/549
[52] U.S. Cl. ..................................... 435/174; 435/176; 435/181; 436/518; 436/524; 436/532; 530/810; 530/811; 530/816
[58] Field of Search ............... 435/176, 177, 180, 181, 435/182; 436/518, 524, 532; 530/810, 811, 816

[56] References Cited

U.S. PATENT DOCUMENTS

| | | | |
|---|---|---|---|
| 3,669,841 | 6/1972 | Miller | 195/63 |
| 4,177,038 | 12/1979 | Biebricher et al. | 435/179 X |
| 4,637,861 | 1/1987 | Krull et al. | 204/1 T |
| 4,824,529 | 4/1989 | Thompson et al. | 204/1 T |
| 4,927,879 | 5/1993 | Pidgeon | 525/54.1 |
| 4,931,498 | 6/1990 | Pidgeon | 525/54.1 |
| 5,102,798 | 4/1992 | Guiseppi-Elie | 435/177 |

OTHER PUBLICATIONS

Kallury, et al., Analytica Chimica Acta, vol. 225, 1989, pp. 369–389.

*Primary Examiner*—David M. Naff
*Attorney, Agent, or Firm*—Juliusz Szereszewski

[57] ABSTRACT

Enzymes and certain other bioactive substances are immobilized on solid substrates which have sufficient functional groups such as hydroxyl or carboxyl. The bioactive substances are linked to the substrates through spacer compounds having a long open alkyl chain with 7–18 carbon atoms and also through phospholipid intermediates. The spacer compound is chemically linked to the substrate. The phospholipid is covalently linked to the spacer compound. Immobilized bioactive substances of the invention exhibit a marked increase in activity and stability. In a preferred embodiment, immobilized enzymes having a high degree of resistance to thermal inactivation are prepared.

20 Claims, 4 Drawing Sheets

IMMOBILIZATION OF BIOLOGICALLY ACTIVE PROTEIN ON A SUPPORT WITH A 7-18 CARBON SPACER AND A BIFUNCTIONAL PHOSPHOLIPID

This invention relates to the preparation of immobilized enzymes with a high degree of resistance to thermal inactivation through covalent attachment to phospholipid layers, which are already covalently linked to solid supports through long chain spacer molecules. Also included in the invention are processes for the synthesis of appropriately functionalized phospholipids suitable for the dual role of binding to bioactive substances as well as to modified solid supports.

BACKGROUND OF THE INVENTION

Enzymes find extensive applicability in diverse areas such as food processing, enantioselective organic synthesis, production of pharmaceuticals, clinical diagnosis/treatment, extracorporeal affinity chromatography, waste management, environmental analysis/pollution control and biosensors. As industrial catalysts, they offer a number of advantages over conventional chemical catalysts due to their high catalytic activity, substrate specificity, the mild conditions involved in their use, minimal by-product formation and no environmental pollution risk. However the two main disadvantages relating to their utility are their instability and the economic factor. The practical use of enzymes often requires elevated temperatures to increase productivity, prevent microbial contamination, improve the solubility of substrates and reduce the viscosity of the reaction medium. On the other hand, the stability of enzymes is affected by conditions such as heat, contact with chemicals and organic solvents, all of which cause denaturation. Amongst these, heat is by far the most important factor for the loss of the biological activity of enzymes and some correlation exists between thermal stability and other kinds of stabilization such as resistance to proteolysis. Thermal inactivation of enzymes is initiated by the partial reversible unfolding of their native structure which is followed by irreversible configurational/conformational changes. Processes such as aggregation, formation of "scrambled structures", cleavage of disulfide bridges, peptide bond hydrolysis, racemization of amino acid residues, deamidation, dissociation of prosthetic groups, isopeptide bond formation and oxidation of thiol/indole groups have been implicated during heat mediated denaturing of enzymes.

Enhancement of the thermal stability could alleviate most, if not all, of the problems associated with the use of native enzymes for various applications. Thermostabilization strategies followed during the past three decades consist of (i) addition of substances, (ii) chemical modification, (iii) cross-linking, (iv) use of anhydrous solvents (non-aqueous media), (v) protein engineering and (vi) immobilization. Of these, the immobilization technique is the most extensively used one for imparting thermal stability to enzymes. Enzymes immobilized on suitable substrates possess considerable advantages over those used in the soluble phase. They often show marked increase in stability and may be used in bioreactors for continuous processing, thereby cutting down on the costs in comparison with reactors utilizing these biocatalysts in solution. For example, using immobilized aminoacylase, the cost of amino acid production is reduced by 40% as against the soluble enzyme. In addition, immobilized biocatalysts are easily removable from reaction mixtures and have enhanced shelf life.

By definition, an immobilized enzyme is a protein physically localized in a certain region of space or converted from a water-soluble mobile state to a water-insoluble immobile condition. Protocols used for immobilizing enzymes can be categorized according to whether the protein becomes immobile by chemical binding or by physical retention. These consist of (i) binding of enzyme molecules to carriers through covalent bonds, (ii) by adsorptive interactions (physisorption), (iii) entrapment into gels, beads or fibres, (iv) cross-linking or co-crosslinking with bifunctional reagents and (v) encapsulation in microcapsules or membranes. Of these, the adsorptive procedures have become more or less obsolete due to the fact that the surfaces produced are too unstable to withstand mechanical stresses and chemical treatments involved in industrial processes. Immobilization through cross-linking has met with limited success because of the large amounts of enzyme required, the uncontrollable nature of the reaction which may lead to inactivation and the unsuitable mechanical properties of the resulting surfaces. The main disadvantages of the microencapsulation technique are that the molecular weight of the substrate has to be very low to allow diffusion across the membranous barrier and the capsules are very prone to enzyme leakage as they are relatively fragile. Furthermore, the polysaccharide-based polymeric materials used for entrapping enzymes into gels or beads suffer from the fact that strict sterile operating conditions must be maintained to prevent the growth of bacteria and fungii. With acrylamide monomers used for entrapment purposes, the conditions of photopolymerization may generate localized temperatures up to 60° C. causing denaturing of the enzyme. With other polymeric systems, problems of enzyme loading, viability and stability have to be overcome for industrial applications.

Several reviews have appeared in the scientific and patent literature on the available choices of substrates and the protocols for covalently binding enzymes on them. The substrates in vogue range from inorganic materials such as porous glass, ceramics, silica and metal/metal oxides to organic materials such as the natural polymers cellulose, chitin and agarose and synthetic products like acrylates, polyamides, derivatized polystyrene and redox systems like polypyrrole. Biomolecules like the avidin-biotin system or bovine serum albumin are also being utilized. However, because of the problems of microbial growth on organic supports, and the consequent loss of activity, collapse of the structure and product contamination, there has been an increasing interest in the use of inorganic support materials, especially silica, controlled pore glass and ceramics.

The two factors to be considered in the selection of a method for the covalent linkage of an enzyme to a support are: the type of functional groups on the protein through which binding to the support is to be accomplished (and consequently the type of chemical reactions to the employed) and the physical/chemical characteristics of the support material with appropriate reactive functionalities grafted onto their surface. The functional groups on the enzymes which are available for covalent bonding are (1) amino (eta-amino groups of lysine and arginine and the N-terminal amino moieties of the polypeptide chains), (2) carboxyl groups of aspartic and glutamic acid and the C-terminal moieties, (3) phenol rings of tyrosine, (4) sulfhydryl groups of cysteine, (5) hydroxyls of serine, threonine and tyrosine, (6) the imidazole groups of histidine and (7) the indole groups of tryptophan. In practice, most of the covalent coupling reactions involve the amino, carboxy and mercapto moieties on the amino acids in the protein structure. The solid supports, in turn, must carry functional groups such as carboxyl, amino, formyl, epoxy, halo (chloro or bromo) and hydroxyl. A majority of solid supports either carry hydroxyls on their surfaces or can be easily modified by chemical or electrochemical means to introduce such hydroxylic groups.

Chemical reactions most commonly used for the interaction of the functionalities in the enzyme with those on the support materials consist of (1) the nucleophilic displacement of the surface hydroxyls on the supports activated with a sulphonyl chloride, 2-fluoro pyridinium tosylate or cyanuric chloride by the amino group on the protein, (2) nucleophilic addition of the protein amino group to a surface hydroxyl on the support which is activated with cyanogen bromide or carbonyldiimidazole or a chloroformate; or an analogous nucleophilic addition of the protein amino group to a carboxyl on the support surface which is activated as its N-hydroxysuccinimide ester, azide or with a diimide, (3) electrophilic addition of a diazonium functionality formed from an aromatic amino moiety on the support to the tyrosine residues on the enzyme, (4) electrophilic addition of the mercapto group on the cysteine moiety of the enzyme to a maleimide function introduced onto the surface of the support, and (5) cross-linking a surface amino group on the support to an amino group on the enzyme with a bifunctional reagent such as glutaraldehyde.

The thermal stability of enzymes covalently attached to support materials is significantly enhanced in comparison with the native enzyme. For example, Hayashi et al. (J. Appl. Polym. Sci. 1992, 44, 143) have observed that papain immobilized on polymethyl L-glutamate exhibited an activity up to three times higher than the native enzyme when maintained at 70° C. in buffer solution for one hour. The free papain loses 90% of its initial activity at 75° C. within 45 minutes. Raghunath and coworkers (Biotechnol. Bioeng. 1984, 26, 104) have demonstrated that urease immobilized on collagen-poly(glycidyl methacrylate) graft copolymer support was thermally stable up to 70° C. and 40 days when stored at 4° C. in a buffer solution. Davidenko et al. (Chem. Abstr. 1985, 102, 127894) have reported that urease adsorbed on carbon fibres is stable up to 65° C. and retained 90% of its activity when stored for a month at 4°-5° C. Thermal stabilization up to 70° C. in buffer solutions was also reported for chymotripsin by multi-point covalent attachment to aldehyde-agarose gels (Guisen et al. Biotechnol. Bioeng. 1991, 38, 1144) and for glucoamylase on periodate oxidized dextran (Lenders and Chricton, Biotechnol. Bioeng. 1988, 31,267). Asakura et al. (Polym.-Plast. Technol. Eng. 1989, 28, 453) immobilized alkaline phosphatase on Bombyx mori silk fibroin by cyanogen bromide and diazo coupling methods and have shown that while the free enzyme was totally deactivated at 65° C., the enzyme coupled by the diazonium procedure retained 30% of its activity, in comparison with 10% for the cyanogen bromide-modified product. Yabushita and coworkers (Chem. Pharm. Bull. 1988, 36, 954) have shown that urokinase immobilized on an ethylene-vinyl acetate copolymer matrix retained more than 50% of its initial activity when kept for 8 hours at 45° C., while the soluble enzyme lost almost all of its activity in 3 hours.

Margolin and coworkers (Eur. J. Biochem. 1985, 146, 625) effected a comparative evaluation of the stability and activity of enzymes immobilized on water-soluble and water-insoluble supports. Employing poly (N-ethyl-4-vinyl pyridinium bromide) (a polycationic support) and poly (methylacrylic acid) (a polyanionic support) for immobilizing a series of enzymes, these authors showed that pronounced thermal stabilization of penicillin amidase and urease could be achieved only if these enzymes are on the precipitated supports (in the insoluble form) and covalently attached to the polyelectrolyte nucleus. Thus, the thermal stability of polyelectrolyte complex-bound penicillin amidase increased seven-fold at pH 5.7, 60° C. and three hundred-fold at pH 3.1, 25° C., compared to the native enzyme. For urease, the thermal stabilization increases twenty-fold at pH 5, 70° C.

The role of phospholipids as protective agents for maintaining the activity of antibodies, enzymes and receptors is well-documented. There is considerable evidence concerning the requirement of a lipid environment for sustaining the activity of enzymes. For example, it has been shown that a lipid-modified glucose oxidase enzyme electrode offers greater selectivity and stability for the analysis of glucose. Phospholipids may act as modulators of enzymatic reactions in addition to their role as obligatory cofactors for some membrane enzymes. Thus, it was shown (Niedzwiecka et al., Acta Biochim. Biophys. Hung., 1990, 25,47), that the purified lymphocyte 5'-nucleotidase reconstituted into lipid bilayer demonstrates remarkable stability on storage at 4° C. The liposome incorporated enzyme from chicken gizzard is five times more stable at 56° C. than the enzyme in the detergent solution, indicating that the phospholipids play a role in preventing the denaturing process.

Rosenberg, Jones and Vadgama (Biochim. Biophys. Acta 1992, 1115, 157) encapsulated glucose oxidase in liposomes and found that electrodes coated with a nitrocellulose membrane carrying these liposome-enzyme formulations exhibited extended linear range of response. The enzyme activity was found to be partially dictated by the liposomal bilayer permeability, and therefore, the enzyme affinity for its substrate could be regulated by using liposomes prepared from different lipids such as dimyristoyl, dipalmitoyl and distearoyl-phosphatidylcholine. It has also been shown by Kotowski and Tien (Bioelectrochem. Bioenerg. 1988, 19, 277) that glucose oxidase could be covalently immobilized on a polypyrrole-supported bilayer lipid membrane surface and the enzyme-substrate reaction could be followed by cyclic voltammetry. The phospholipid functions as an electric switch during this analysis, besides supplying the natural biomembrane-type environment to the enzyme.

Besides thermal inactivation, the extent of activity exhibited by an immobilized enzyme is also dependent upon aspects such as the chemical procedure used to effect immobilization, the spacer chain length and the pH of the buffering medium in which the enzyme-substrate reactions are carried out. For example, Comfort et al. (Biotechnol. Bioeng. 1988, 32, 554) evaluated the immobilization yields of heparinase and bilurubin oxidase on agarose and acrylic beads activated by four different reagents, viz. cyanogen bromide, carbonyldiimidazole, oxirane and tresyl chloride, respectively. They found that while heparinase was bound in 90% yield (with 50% active enzyme) by the cyanogen bromide method, bilurubin oxidase was preferentially linked. (50-55% maximum yield, with 25-30% active enzyme) by the tresyl chloride and oxirane displacement. However, in both cases, nearly 40-50% of the immobilized enzymes were leached out when allowed to stand in buffer for a short time. Przybyt and Sugier (Anal. Chim. Acta 1990, 239, 269) investigated the activity of urease immobilized on oxidized tungsten electrodes by electrochemistry. The covalent binding protocol followed by these authors consisted of initially silanizing the metal oxide surface with gamma-aminopropyltriethoxysilane and then cross-linking the enzyme with either cyanuric chloride or hexamethylene diisocyanate or glutaraldehyde. They found that the lifetime of the enzyme electrodes with the cyanuric chloride linker was only one day. In comparison, the lifetimes of electrodes prepared by employing glutaraldehyde and the diisocyanate cross-linkers were 29 and 22 days, respectively. The life-time of the enzyme electrode, obtained by the direct cross-linking of the metal oxide surface with the enzyme through hexamethylene diisocyanate (without prior silanization) was 19 days. Furthermore, these authors noted profound effects on the electrode response due to factors such a the nature of the buffer, its concentration and ionic strength.

The importance of the spacer chain length towards the retention of the activity of an immobilized enzyme on a given surface has been demonstrated by several groups of workers. For instance, Kennedy and Cabral (in *Methods in Enzymology*, Vol. 135, pp. 117-130, Academic Press, San Diego, 1987) examined the linking of glucoamylase to control pore glass activated with titanium tetrachloride. The substrates were initially treated with ammonia (no carbon spacer), 1,2-diaminoethane (a two-carbon spacer) and hexamethylene diamine (a 6-carbon spacer) and then cross-linked with the enzyme through glutaraldehyde. The six carbon spacer-carrying substrate exhibited an activity retention of 12% relative to the activity of the soluble enzyme, while the figures were 1.5% and 3.2% for the no carbon and two carbon spacer, respectively. Jayakumari and Pillai (J. Appl. Polym. Sci. 1991, 42, 583) observed that the direct coupling of papain to carboxylated polystyrene yielded only 5% active enzyme, while binding of the same enzyme to the same support through glutaric anhydride cross-linker produced 30% of active enzyme. However, the maximum activity retention (54%) was obtained when papain was linked to hydroxymethyl polystyrene through polyethylene glycol (PEG 600) cross-linker. These authors also demonstrated that increasing cross-link densities decreased the total immobilization yields as well as the amount of active enzyme. Furthermore, rigid supports lowered total/active enzyme yields in comparison with flexible supports. Schuhmann et al. (J. Amer. Chem. Soc. 1991, 113, 1394) showed that the electrical communication between the redox centres of glucose oxidase and vitreous carbon electrodes is more effective when a long chain diamine was used to cross-link the aldehyde functionalities of ferrocene and those of glucose oxidase obtained by the oxidation with periodate. Reduction of electron-transfer distances between the redox centre of the enzyme and the peripherally bound ferrocene relay and between the relay and the electrode due to penetration of the relay to a sufficient depth by the enzyme was postulated to be responsible for their observations. Kobayashi et al. (J. Colloid Interface Sci. 1991, 141, 505) have reacted microfine magnetic particles of magnetite with APTES and then cross-linked the surface with a protease; thermolysin, with glutaraldehyde. They also utilized omega-aminohexylaminopropyltrimethoxysilane, 4-aminobutylaminopropyltrimethoxysilane and 2-aminoethyl-aminopropyltrimethoxysilane and showed that maximum enzymatic activity was exhibited by the hexyl-silane (50% higher than with APTES).

The report of Williamson et al. (Anal. Letters 1989, 22, 803), however, contradicts the above findings on the spacer length, when an antibody, rather than an enzyme, is immobilized to a support. These authors covalently attached anti-$T_2$ mycotoxin monoclonal antibodies on quartz fibres by three techniques. The first two consist of the activation of the surface hydroxyls of quartz with p-toluene sulphonyl chloride or p-nitrophenylchloroformate, followed by the direct attachment of the antibody. The third method involves initial silanization of quartz with APTES followed by cross-linking of the antibody with glutaraldehyde. Almost the same amount of activity was found to be exhibited by the antibody on all of the above three surfaces. However, the thermal stability of the antibody on the APTES-modified surface at 50° C. was considerably better than the antibody surfaces prepared with the other two reagents. Significantly, treatment of the sulphonyl chloride or chloroformate activated quartz with hexamethylene diamine, prior to the immobilization of the antibody with glutaraldehyde, did not improve the activity of the bound antibody, in spite of the six-carbon spacer.

The above brief summary of the thermal and a thermal factors responsible for the deactivation of enzymes indicates that even immobilized enzymes are not stable above 60°-70° C. In a number of instances, nearly 50% of the immobilized enzyme is leached out by washing with a buffer or detergent. Use of cross-linkers during the immobilization of the enzymes also has a detrimental effect on the retention of the activity by the immobilized biomolecules. Recent advances in the isolation of thermostable enzymes utilize thermophilic bacteria and considerable thermal stability has been claimed for the enzymes made by this route. However, a recent report by Brosnan and coworkers (Eur. J. Biochem. 1992, 203, 225) demonstrates that alpha-amylase isolated from *Bacillus stearothermophilus* is irreversibly deactivated at 90° C. in 1.9 minutes at pH 5.0.

Although a large number of publications in documented literature have clearly indicated that phospholipids exert a stabilizing effect on the activity of enzymes, enzyme preparations so far known have only utilized encapsulations in phospholipid liposomes. In two earlier patents (U.S. Pat. No. 4,824,529 {1989] and U.S. Pat. No. 4,637,861 [1987]), as well as in a recent publication (Anal. Chim. Acta 1989, 225, 369), we have demonstrated that phospholipids can be covalently attached to different kinds of supports. As analogues of natural biomembranes, these phospholipids are expected to impart greater stability than hitherto known to enzymes, if the two bio-entities could be covalently linked. It is envisaged that the combination of a suitable spacer chain and immobilization to a support through a phospholipid would enable the formation of thermally very stable enzyme systems with extended operational and storage stabilities in the solid state (without any buffers), for a variety of applications.

It is therefore an object of the present invention to provide new compounds suitable as spacers as well as linkers for the covalent immobilization of enzymes and other biologically active substances either directly or through an intermediate compound, onto a substrate.

It is a further object of the present invention to provide new phospholipids suitable for covalent binding to the substrate through a spacer compound and to the bioactive molecule.

It is another object of the present invention to provide preparations comprising immobilized biologically active substances, e.g. enzymes, bound to the substrate through the spacer compounds and optionally also through the phospholipids.

It is still another object of the present invention to provide methods for the preparation of the spacers and phospholipids utilized in the present invention.

SUMMARY OF THE INVENTION

According to the invention, it is proposed to link enzymes (or other biologically active molecules) to selected substrates through certain spacer compounds, for example alkoxysilanes and preferably also through phospholipid intermediates which are bound to the silanized substrate and to the biologically active substance.

Preferably, the substrate is a solid material having sufficient functional groups selected from hydroxyl, carboxylic, amino, mercapto and aldehyde groups to enable the spacer compound (alkoxysilane or a diamine or a dicarboxylic acid) to be attached to the substrate.

The substrate may be an inorganic material such as a metal, semiconductor (silica or quartz) or ceramic (e.g. alumina); an organic polymer (either a naturally occurring material such as cellulose or chitin or agarose, or a synthetic product, like modified teflon) and a biomolecule, e.g. protein or whole cell, provided that the above-defined functional groups are present or can be incorporated onto the surface of this substrate. On metallic substrates, hydroxyl groups can be incorporated by oxidation and subsequent hydration.

The biologically active substances, referred to herein also as bioactive substances, suitable for the purpose of the present invention, are enzymes, antibodies, antigens and other proteins, i.e. compounds with polypeptide structure. Certain other molecules such as DNA or hormones (with polypeptide structure) are also suitable.

The enzyme or another bioactive substance is covalently linked to the phospholipid as opposed to encapsulation in liposomes proposed in the prior art.

Accordingly, this invention relates, in one aspect, to new preparations comprising, in general terms, a solid substrate and a biologically active substance linked covalently to the substrate through a spacer compound having 7-18 carbon atoms in its alkyl chain.

The spacer compound may be an alkoxysilane, a dicarboxylic acid or a diamine.

In another aspect, the invention relates to new preparations comprising a substrate, a phospholipid covalently linked to the substrate through a spacer compound having 7-18 carbon atoms in its alkyl chain, and a bioactive substance covalently linked to the phospholipid.

In yet another aspect, the present invention proposes a new method of making the above-defined structures, the method comprising:

(a) providing a selected solid substrate having sufficient functional groups selected from hydroxyl, carboxyl, amino, mercapto and aldehyde on its surface, (b) binding an alkoxysilane (or a long chain dicarboxylic acid or a long chain diamine) to the functional groups of the substrate, and, (c) binding the biologically active substance to said alkoxysilane (or other spacer).

Alternatively, the method comprises the following steps:

(a) providing a selected solid substrate having the required functional groups selected from carboxyl, hydroxyl, amino, mercapto or aldehyde on its surface, (b) binding a spacer compound to the functional groups of the substrate, (c) binding a phospholipid to the spacer molecule, and (d) binding a biologically active substance to the phospholipid.

In a preferred embodiment of the invention, the bioactive substance is an enzyme. Urease was selected for laboratory tests, but the invention is not limited thereto.

Where a phospholipid is a part of the immobilized structure of the invention, a number of spacer compounds may be utilized for bonding the phospholipid to the support. Alkoxysilanes with an open chain having from 7 to 18 carbons atoms, aliphatic dicarboxylic acids and diamines with similar alkyl chains can be used as the spacer compounds.

BRIEF DESCRIPTION OF THE DRAWINGS

In the drawings which illustrate the invention in more detail.

DETAILED DESCRIPTION OF THE INVENTION

Experimental

Silicon wafers were used as substrates. The wafers (10 cm in diameter, p-doped, natural oxide grown) were purchased from Avrel Colo., Santa Clara, Calif. Silica gel Davisil (trademark), Grade 645, 60-100 mesh, 150 Å (angstrom), 99+% purity) was obtained from Aldrich.

All solvents were reagent grade samples further purified by drying with an appropriate drying agent and distilled prior to use. The following products: glutaric anhydride, 10-undecylenic acid, 11-aminoundecanoic acid, chloroplatinic acid, t-butyldimethylsilylchloride, triethoxysilane, dimethylaminopyridine, N-hydroxysuccinimide, carbonyldiimidazole, dicyclohexylcarbodiimide, di-t-butylcarbonate, sebacoyl chloride, aminopropyltriethoxysilane and trifluoroacetic anhydride were purchased from Aldrich.

Glycerophosphoryl choline cadmium chloride complex, ethyldimethylaminopropyl carbodiimide, Urease (U2000) were purchased from Sigma.

Lyso 1-palmitoyl phosphatidylethanolamine was supplied by Avanti, Urease (URE3) was supplied by Biozyme, Urease substrate solution by J. D. Biologicals and aminopropyldimethylethoxysilane by Petrarch.

Synthesis of Omega-Functional Alkyl Triethoxysilanes

1. Preparation of 11-triethoxysilylundecanoic acid methyl ester:

a) 10-Undecylenic acid (20 mmoles) was dissolved in methanol (25 ml) and concentrated hydrochloric acid (0.5 ml) added. The mixture was refluxed for five hours, the excess methanol distilled off and the residue treated with cold sodium bicarbonate solution (5% aq., 200 ml). The crude methyl ester was extracted with ether, the ether layer washed with water, dried with magnesium sulphate and concentrated on a rotary evaporator to yield a colorless liquid (yield almost quantitative). Distillation of this product under vacuum gave the pure ester, b.p. 104°–5° C./0.1 mm.

b) Hydrosilylation—The pure methyl ester (2 g) was treated with triethoxysilane (3 ml) under nitrogen with the addition of chloroplatinic acid (10 mg). After stirring at room temperature for 12 hours, the mixture was refluxed for 2 hours. The excess silane reagent was removed under vacuum and the residue extracted with pentane under nitrogen. The extract was filtered and the filtrate concentrated under vacuum to yield the desired product as a colorless liquid Yield 3.5 g). FABMS: MH+, m/z 363, [MH-EtOH]+, m/z 318 (100%); FTIR: $\nu$C=O 1731 cm$^{-1}$, $\nu$Si-O 1102, 1081 cm$^{-1}$.

2. Preparation of 11-triethoxysilyl undecylenic acid t-butyldimethysilyl ester:

a) 10-Undecylenic acid (20 mmoles) was dissolved in DMF (20 ml) to which t-butyldimethylsilyl chloride (4.5 g) and imidazole (100 mg) were added. The mixture was stirred at room temperature under nitrogen for 24 hours. Excess solvent and silane reagent were removed under vacuum and the residue extracted with pentane. The pentane extract was dried and concentrated on a rotary evaporator to yield the crude ester, which was purified by distillation under vacuum, b.p. 110°–112° C./0.1 mm, yield quantitative. FTIR: $\nu$C=O 1716 cm$^{-1}$.

b) Hydrosilylation—This reaction was carried out under the same conditions as described under 1b. The product was characterized by FABMS: MH+, m/z 449 (10%), [MH-EtOH]+, m/z 403 (100%); FTIR: $\nu$C=O 1716 cm$^{-1}$, $\nu$Si-O 1102 and 1088 cm$^{-1}$.

Generation of the Omega-Carboxylic Silylated Surfaces 1 and 2

Figure 1:
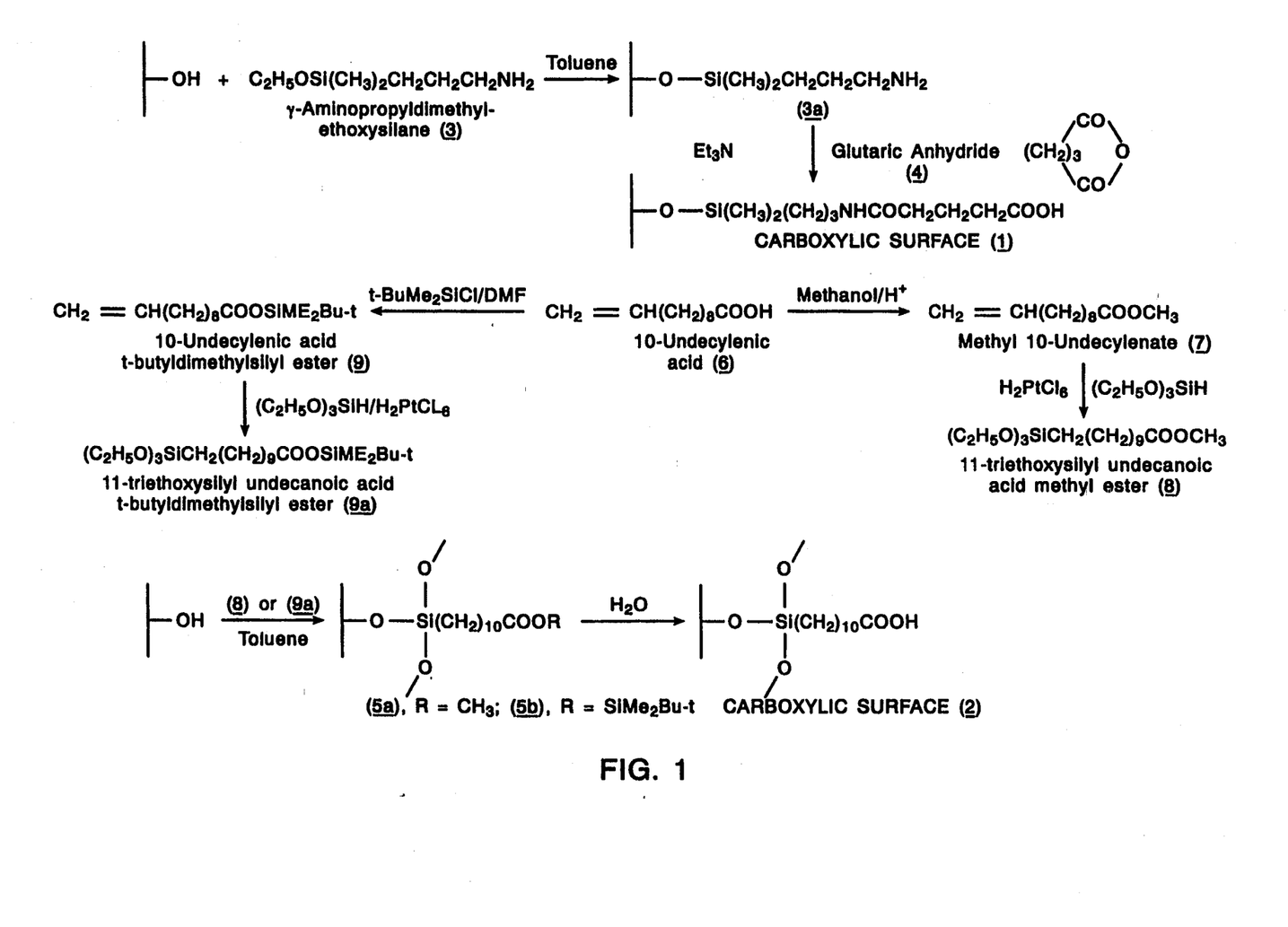
FIG. 1 is a representation of chemical reactions leading to the generation of silanized surfaces.

1. Formation of the carboxylic surface 1 (see FIG. 1)

a) Silanization of silica surfaces by 3-dimethylethoxysilyl 1 propanamine was carried out by treating the cleaned surfaces with a solution of gamma-aminopropyldimethylethoxysilane 3 (2% in toluene, 20 ml) and refluxing for six hours under nitrogen. The substrates were then removed and washed with chloroform, methanol and acetone in that order. Surface characterization was effected by XPS and ellipsometry.

b) Treatment of the silanized surface with glutaric anhydride—the above substrate 3a was suspended in THF (25 ml) and glutaric anhydride 4 (500 mg) was added. The mixture was refluxed under nitrogen for 12 hours, the substrate removed from the solution and washed extensively with alcohol. The resulting surface was characterized by XPS and ellipsometry.

2. Formation of the carboxydecyl dimethylsilylated surface 2

A. From 11-triethoxysilyl undecanoic acid methyl ester 8 (FIG. 1)

a) Silanization of silica substrates with the methyl ester 8

The substrate was suspended in toluene containing the methyl ester 8 (2% solution) at room temperature under nitrogen overnight. It was then removed and washed thoroughly with dichloromethane and dried under vacuum for several hours.

b) Hydrolysis of the methyl ester function—after sodium hydroxide, sodium carbonate, potassium t-butoxide were found to cleave the surface-to-silane siloxane bond, it was attempted to use a non-basic approach. The methyl ester-containing substrates were refluxed for 24 hours with lithium iodide (200 mg) in DMF (20 ml). The substrates were recovered and washed thoroughly with distilled water and vacuum dried before XPS and ellipsometric analysis. Alternatively, the methyl ester moiety can be removed by refluxing with trimethylchlorosilane (5 ml) and sodium iodide (500 mg) for six hours.

B. From 11-triethoxysilyl undecanoic acid t-butyldimethylsilyl ester (9a):

a) silanization of silica substrates with the ester 9a—this reaction was carried out at room temperature under nitrogen in toluene solution as described under the methyl ester 8. Surface analysis was done by ellipsometry and XPS.

b) hydrolysis of the t-butyldimethylsilyl ester moiety—the hydrolysis of the silyl ester was accomplished by suspending the substrate from reaction a) in aqueous methanolic hydrochloric acid (1:1, 10%, 10 ml) for three hours. The substrate was washed copiously with water and dried. Surface analysis was done by the usual techniques.

Immobilization of Urease on the Carboxyl-Functionalized silanized surfaces 1 & 2

A. Direct Immobilization

The carboxylic surface 1 or 2 (100 mg) was suspended in distilled water and treated with EDC (5 mg) for 12 hours, the supernatant liquid decanted off and the substrate treated with urease (1 mg) in distilled water (1 ml) for a period of 48 hours at 5° C. The supernatant liquid was carefully drawn off and its enzymatic activity determined by spectrophotometry after dilution to 10 ml. The substrate was thoroughly washed with distilled water and kept under water in the refrigerator.

B. Activation with N-Hydroxysuccinimide and immobilization.

a) Treatment of the surfaces 1 and 2 with NHS—the carboxylic surfaces 1 and 2 were suspended in THF (5 ml) and DCC (10 mg) in the same solvent was added. The mixture was stirred under nitrogen at room temperature for 24 hours. The substrates were washed thoroughly with methanol and then with distilled water.

b) Reaction of the NHS-activated substrates with urease—the activated substrate (100 mg) was suspended in distilled water (1 ml) and urease (1 mg) added. The mixture was set aside for 48 hours at 5° C., the supernatant liquid carefully drawn off and tested spectrometrically for residual enzyme activity. The substrate was washed well with water and stored in the fridge.

C. Activation with carbonyldiimidazole prior to immobilization.

a) Treatment with CDI—the carboxylic substrates 1 and 2 were suspended in THF (5 ml) and CDI (20 mg) was added. After standing for two hours at room temperature, the substrates were washed with THF and used immediately.

b) Reaction of the CDI-activated substrates with urease—the CDI treated substrates (100 mg) were suspended in water (1 ml) and urease (1 mg) added. The mixture was allowed to stand for 12 hours at 5° C., the supernatant was removed carefully, diluted ten times and analysed spectrophotometrically. The substrates were washed with water and stored in the refrigerator.

Synthesis of Bifunctional Phosphatidylcholines and Their Covalent Binding to Carboxy Functionalized Silanized Substrates and to Enzymes.

A. Preparation of protected omega-functional fatty acid reagents.

a) 12-trifluoroacetoxy dodecanoyl chloride—12-hydroxydodecanoic acid (2.2 g) was dissolved in THF (25 ml) and the solution treated with trifluoroacetic anhydride (3 ml) in the presence of a few drops of pyridine. The mixture was stirred overnight at room temperature under nitrogen and then subjected to vacuum to remove solvent and other volatile organics. The residue was extracted with ether, the organic layer washed with water, dried and concentrated on a rotary evaporator to furnish the trifluoroacetate as a colourless oily liquid (CIMS, MH+, m/z 313).

The acid chloride of the above acetate was obtained by stirring it in THF solution with thionyl chloride for two hours. The solvent and excess reagent were removed under vacuum and the residue used as such for the next step (FTIR: $\nu C=O$ 1805 cm$^{-1}$ and 1740 cm$^{-1}$).

b) 11-N-t-butoxycarbonylamino-undecanoic acid—this N-protected acid was obtained by reacting 11-aminoundecanoic acid (10 mmoles) dissolved in 0.1M potassium hydroxide (till neutral) with di-t-butylcarbonate (1.2 molar equivalents) at 0° C. with stirring for two hours. The solution was rendered slightly acidic with acetic acid and the precipitated N-BOC derivative filtered off, washed with plenty of water and dried in a vacuum desiccator (yield 80%)—FTIR: $\nu C=O$ 1728, 1708 and 1665 cm$^{-1}$.

B. Synthesis of 1-(12-trifluoroacetoxydodecanoyl)-sn-glycero-phosphatidylcholine (15)

Glycerophosphorylcholine cadmium chloride complex (1 mmole) was treated in aqueous methanol with silver carbonate and the precipitated inorganic material was filtered off. The filtrate was concentrated under vacuum and the residual free lipid dried by repeated evaporation with dry benzene. The dried free glycerophosphorylcholine (1 mmole) was reacted with 12-trifluoroacetoxy-dodecanoyl chloride (1.1 mmole) in pyridine medium at 0° C. for 24 hours. The pyridine was removed under vacuum and the residue extracted with chloroform. Drying and concentration on the rotary evaporator furnished the title lyso lipid 15 (FIG. 3) which was characterized by proton NMR.

C. Synthesis of 1-(12-trifluoroacetoxydodecanoyl)-2-(11-BOC-aminoundecanoyl)-sn-glycerophosphorylcholine 16.

The above lyso lipid (0.8 mmole) was stirred in dichloromethane solution with 11-(N-BOC-amino)-undecanoic acid (1 mmole), DCC (1 mmole) and DMAP (1 mmole) for 48 hours under nitrogen. The mixture was concentrated on a rotary evaporator and the residue extracted with ether to remove ether-solubles. The ether solubles were treated with chloroform and the chloroform solution passed through Rexyn I-300 (trademark). The lipid 16 (FIG. 3) was further purified by chromatography over silica gel. The product was characterized by proton NMR.

D. Deprotection of the N-BOC group on the sn-2 chain of the choline 16.

The diacyl lipid 16 was stirred in dichloromethane solution at 0°-5° C. with trifluoroacetic acid (1 ml) for two hours. The product 17 (FIG. 3) was isolated by concentration under vacuum and used immediately for the next step.

E. Covalent binding of the bifunctional lipid 17 to the carboxylic supports 1 and 2.

The above lipid 17 was reacted with the NHS-activated supports 11 (FIG. 1) in chloroform medium overnight at room temperature under nitrogen. The resulting substrate was washed thoroughly with methanol to remove any unbound lipid and characterized by ellipsometry.

F. Deprotection of the trifluoroacetoxyl group on the sn-1 chain.

The above substrate 18 with the covalently bound lipid was treated with sodium bicarbonate (5% aq., 20 ml) for three hours at room temperature. The resulting substrate 19 was washed well with water.

G. Oxidation of the omega-hydroxyl in 19.

The substrate 19 was suspended in potassium permanganate (5% aq., 10 ml) and warmed at 50° C. on a water bath for three hours. The substrate (20) was recovered and washed extensively with water and characterized by XPS.

H. Activation of the compound 20 with NHS and condensation with urease.

The carboxylic support 20 (100 mg) was treated with NHS (100 mg) in chloroform for 12 hours at room temperature in the presence of DCC (100 mg). The resulting substrate was washed extensively with methanol and resuspended in distilled water (1 ml). Urease (1 mg) was added and the mixture set aside for 48 hours at 5° C. The clear supernatant was carefully recovered, diluted ten times and analysed spetrometrically. The substrate 21, with both the lipid and enzyme attached, was washed well with water and stored in a refrigerator.

Lipid and Urease Attachment to the Carboxylic Supports 1 and 2 by an Alternate Route Utilizing Phosphatidylethanolamines.

a) Covalent binding of 1-palmitoyl-sn-glycerophosphatidyl-ethanolamine to NHS-activated carboxylic supports 11: the NHS-activated substrates 11 (FIG. 2) were suspended in chloroform and reacted with 1-palmitoyl-sn-glycerophosphatidylethanolamine (10 mg) for 12 hours at room temperature. The substrate 23 (FIG. 4) was recovered and washed well with methanol, dried and characterized by XPS.

b) Condensation of 23 with sebacoyl chloride—the substrate 23 was suspended in THF and treated with sebacoyl chloride (20 mg) in the presence of a few drops of triethylamine and stood overnight under nitrogen. The resulting substrate was suspended in sodium bicarbonate (1% aq., 10 ml) for two hours and washed with water to yield 24.

c) Activation of the carboxyl of 24 and coupling with urease—the substrate 24 was activated in the usual manner with NHS in a chloroform solution. The resulting substrate was suspended in 1 ml water containing urease (1 mg) for 48 hours at 5° C. and the supernatant liquid was removed from the substrate carefully for analyzing residual enzyme spectrophotometrically. The substrate 25 or 26 was recovered and stored in a refrigerator.

Spectrophotometric Measurements

Calibration curves correlating the concentration of the enzyme urease with the absorbance of the pH sensitive indicator dye bromocresol purple present in the substrate solution were initially obtained. For this purpose, a standard solution of urease (1 mg in 100 ml distilled water) was prepared and 2 ml of this solution mixed with 1 ml of substrate solution in a UV cell. The absorbance of this mixture at 588 nm was read off after allowing it to stand for 15 minutes. The procedure was repeated with 0.5 ml increments of the urease solution up to a maximum of 7 ml. A blank experiment without the enzyme was also done to ascertain the absorbance of the substrate solution at the same concentration and wavelength 588 nm. Each of the silica substrates on which the urease was immobilized (two without the lipid and two with the lipid) was suspended in 1 ml of water and 1 ml of the substrate solution was added. After standing for 15 minutes, the solution was diluted to 10 ml with water and its absorbance read off.

The absorbances of the filtrates from the enzyme immobilization reactions were also determined in a similar fashion after diluting them to 10 ml (including the volume of the substrate). The concentration of the non-immobilized enzyme was obtained from the calibration curve recorded. Since the enzyme used for the immobilization reactions in each case was 1 mg, subtraction of the concentration of the non-immobilized urease from this gives the amount of urease immobilized on the substrates.

XPS Characterization

The surfaces were analyzed by means of X-ray photoelectron spectroscopy. The results are presented in Table I.

Instrumentation

The positive FAB mass spectra were recorded on a VG 70-250S double-focussing mass spectrometer operating at 8 kV and equipped with a VG 11-250 data system. The FAB beam employed xenon atoms of about 8 kV generated by an Ion Tech saddle field gun. Nitrobenzyl alcohol was used as the matrix for the spectra.

Ellipsometric measurements were made on an Auto EL-2 Ellipsometer, Rudolph Research, Flanders, N.J., using a He-Ne laser with a wavelength of 6328 Å and as incident angle of 70°. Data were analyzed on a HP85 computer. A refractive index of 1.5 for the surface silane film was assumed in the calculations.

X-ray photoelectron spectra were recorded on a Leybold LH200 machine with excitation by non-monochromatized Mg $K_\alpha$ radiation. An excitation voltage of 1253.6 eV and a detector voltage of 2.65 eV along with an emission current of 25 $\mu$A were utilized. Take-off angles of 90° were employed for both low and high resolution experiments. The spot size employed was 4×7 mm. Pass energies of 192 eV and 48 eV were made use of for broad and narrow region scans respectively. The intensities reported were corrected for Scofield factors.

Spectrophotometric measurements were carried out on a Hewlett Packard 8452A diode array spectrophotometer at 2 nm resolution using the software supplied by the manufacturer.

Results and Discussion

Generation of Carboxy-Functional Silanized Surfaces

Silica has been selected as the support for the immobilization of enzymes in the present invention, as a representative of the silicon-based carrier materials such as quartz, controlled pore glass and oxidized silicon chips which are extensively used in biosensory applications. It is well-known that inorganic carriers have an advantage over organic polymeric materials owing to their greater compression resistance and stability of surface structure. Further, granular supports such as porous glass or silica, utilized for affinity chromatography, are characterized by their resistance to acids and organic solvents and to microbial attack, in addition to their rigidity, thermal stability and outstanding hydrodynamic properties.

Some serious disadvantages with the silica-type materials for linkage to biomolecules is their limited binding capacity, non-specific adsorption and denaturation of proteins due to the surface silanol groups. These shortcomings could be eliminated by derivatization of the surface, especially through the silanization reaction. The most commonly employed reagent for this purpose is gamma-aminopropyltriethoxysilane (abbreviated as APTES. listed in the Chemical Abstracts under 3-triethoxysilyl 1-propanamine). The surface amino groups thus generated could be linked to the carboxylic groups on the protein in the presence of a carbodiimide reagent. Alternately, these surface amino moieties could be cross-linked with the amino groups on proteins with reagents like glutaraldehyde, cyanuric chloride or a diisocyanate. Of all these procedures, the glutaraldehyde-mediated immobilization of enzymes is the most commonly utilized one. However, there are several shortcomings associated with this protocol which are yet to be addressed. First and foremost, it is known that APTES forms multilayer structures on hydroxylic substrates. The overall structure is dependent upon factors like the amount of surface water, curing temperature, nature of the solvent used for silanization, presence of catalysts and pH of the reaction medium, to mention a few of these factors. It has also been demonstrated that the amino moieties form hydrogen-bonded structures resulting from the partial or total proton transfer from the substrate or silane silanol groups. These authors showed in a 1988 paper that nearly 75% of the amino groups are involved in hydrogen-bonded structures by XPS studies. Further, the mechanism of cross-linking of amino groups by glutaraldehyde is still poorly understood and controversial, since a mixture of products is always produced including Schiff bases, secondary amines, pyridinium-type cross-linkers and many other speculative structures. Moreover, the activity of the immobilized enzymes with the three-carbon spacer supplied by APTES is very low, due to interaction with the support surfaces.

To overcome the above problems posed by APTES, it is now proposed, according to this invention, to design silanizing agents that would unequivocally form well-defined, preferably monolayer-level, structures on hydroxylic surfaces. In addition, it will be more advantageous to have a terminal carboxylic moiety on the silane rather than an amino group, since the former does not require cross-linking agents which can create complications and could be coupled directly to enzymes. According to the invention, it was considered appropriate to develop carboxyl-functionalized silanized substrates. These can be generated by two different techniques. One consists of initially silanizing a hydroxylic substrate with an aminoalkyldimethylsilane and then derivatizing the amino moiety of the surface-bound silane with a dicarboxylic anhydride to generate a spacer-arm carrying a terminal carboxyl group. The second approach involves the synthesis of an omega-ester functionalized alkyl chain-substituted alkoxysilane which can be initially linked to a hydroxylic support through the alkoxyl and then the terminal ester could be hydrolyzed to a carboxylic moiety under mild conditions, not detrimental to the surface-siloxane bond.

As illustrated in FIG. 1., both of the above strategies have been adopted to build carboxyalkyl substituted silanized substrates for the purposes of the present invention. In these experiments, gamma-aminopropyl-dimethylethoxysilane was selected as the supplier of the surface amino group owing to the fact that it can only form one surface siloxane bond with virtually no chance for cross-linking and therefore no multi-layer build-up. However, more drastic conditions were found to be necessary with this silane to effect silanization of hydroxylic substrates like silica or quartz, compared to APTES. This is due to Steric factors presented by the two methyl groups on the silicon atom.

The best conditions were found to be, refluxing a substrate with this reagent for six hours in toluene, followed by thorough washing with a variety of solvents. The next step is the introduction of the carboxyl, which could be achieved by refluxing the silanized substrate 3a (FIG. 1) with glutaric anhydride in THF for several hours to form a five-carbon spacer arm with a terminal carboxylic group (surface 1, FIG. 1).

The alternate approach involves the synthesis of the ester-terminated triethoxysilanes 8 and 9a (FIG. 1) starting from 10-undecylenic acid 6. This unsaturated acid was converted into either its methyl ester 7 or t-butyl-dimethylsilyl ester 9. Both 7 and 9 could be hydrosilylated with triethoxysilane in the presence of chloroplatinic acid catalyst to introduce the terminal triethoxysilyl moiety. The hydroxylic substrates silica or quartz utilized in the current work were silanized with 8 or 9a at room temperature in toluene. The t-butil-dimethylsilyl ester could be readily hydrolysed with dilute hydrochloric acid to yield the carboxylic surface 2 (FIG. 1). On the other hand, the normally applicable basic hydrolytic conditions did not work for hydrolysing the methyl ester surface 5a, since under these conditions, the siloxane bond to the surface was also cleaved. However, refluxing with either lithium iodide in DMF or trimethylchlorosilane/sodium iodide mixture was found to smoothly dimethylate the ester moiety of 5a into the carboxylic surface 2.

Immobilization of urease on the carboxy-functionalized silane surfaces 1 and 2.

Figure 2:
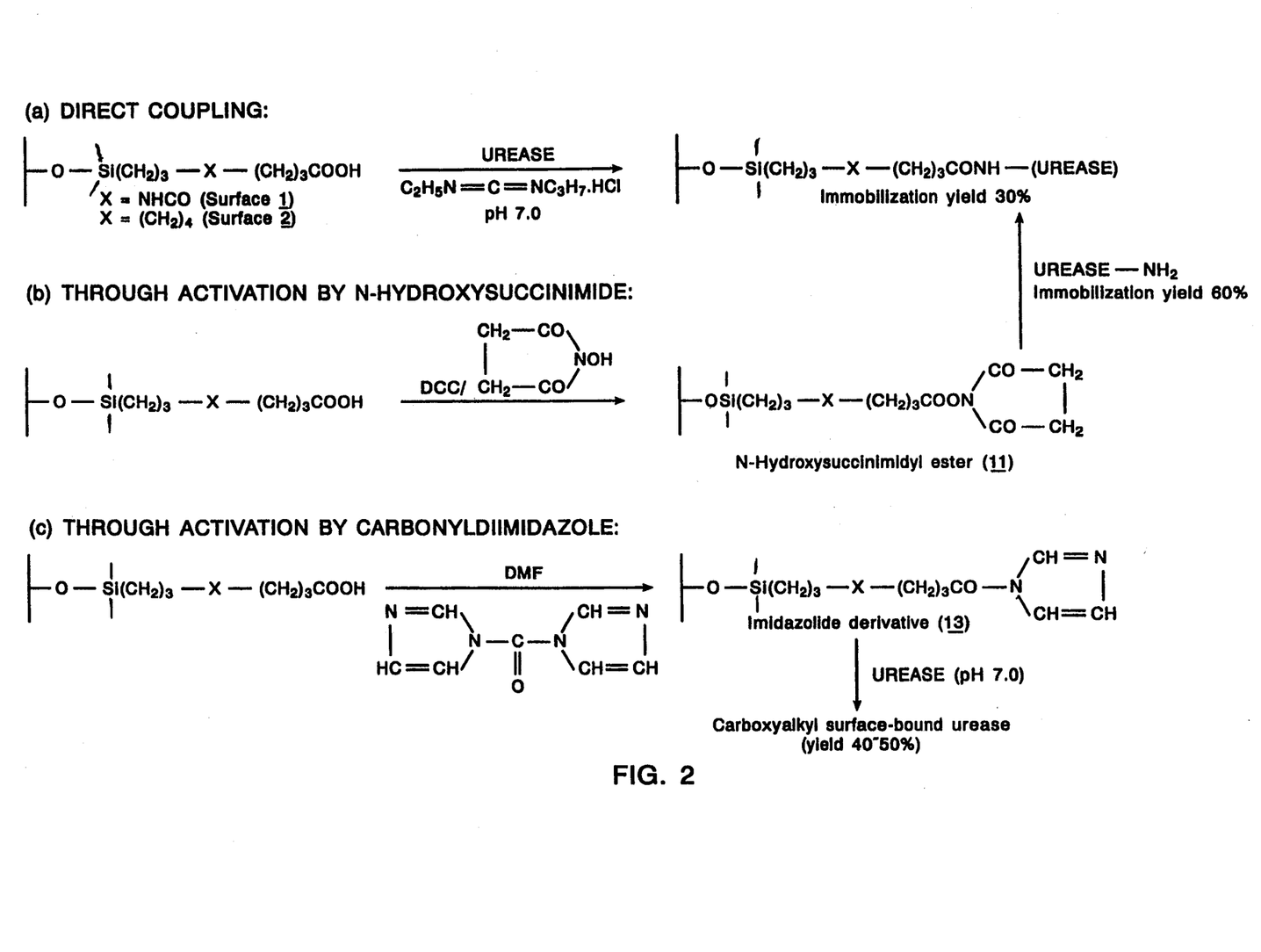
FIG. 2 illustrates the immobilization of an enzyme, urease, on silanized surfaces of FIG. 1, by: a) direct coupling, b) activation by N-hydroxysuccinimide, and c) activation by carbonyldiimidazole.

The amino groups on the lysine residues on the urease are the targets for coupling with the carboxylic substrates 1 and 2. Three different approaches were followed to effect this coupling, as illustrated in FIG. 2. The first approach was the direct one-pot coupling in aqueous medium utilizing the water-soluble ethyldimethylaminopropyl carbodiimide hydrochloride to initially activate the surface carboxyl of substrates 1 and 2. The supernatant liquid was drawn off and the diimide-activated surfaces were treated with urease in water. The excess unbound enzyme present in the solution was estimated by spectrophotometry. The second route consisted of initially activating the surface carboxyls 1 and 2 with N-hydroxysuccinimide and condensation with urease in aqueous medium in the second step.

The third method involved the activation of the surface carboxyls with carbonyldiimidazole and then treatment with urease in aqueous medium.

Determination of the amount of the non-immobilized enzyme indicated that the direct coupling of urease gave about 30% immobilization yield while the figures for NHS and CDI activation methods were 60% and 50% respectively.

It was found that with CDI, the intermediate imidazoles 13 (FIG. 2) are very unstable and have to be used immediately after formation. On the other hand, the NHS esters 11 were reasonably stable over the 24 hour period examined and give better yields than the other two methods. Hence, for the lipid-immobilization procedures, this NHS-activation method was followed.

Synthesis of bifunctional phospholipids and their covalent binding to silanized substrates and to urease.

The covalent attachment of phospholipids to both substrate and enzyme requires the synthesis of lipids with two functional groups, one each on the terminal carbon of both acyl chains. In order that they do not react with each other or simultaneously with the substrate, both should be protected with appropriate protective groups. Moreover, since the head groups of phospholipids are extremely sensitive to strongly acidic or basic conditions, either the introduction of the omega-protected functional acyl chains onto the glycerolphosphocholine skeleton or removal of the protective moieties should be carried out under the mildest possible conditions.

The strategy developed according to the present invention to effect dual binding of phosphatidylcholines to substrate and enzyme consists of introducing an omega-amino moiety onto the sn-2 acyl chain which can be linked to the surface carboxylic group and an omega-protected hydroxy-substituted acyl chain at the sn-1 position which can be oxidized to a carboxyl and bound to an amino group on the enzyme (after the surface binding of the sn-2 chain). In other words, the two functionalities on the lipid consist of an amine which can be linked to the surface and a carboxyl which can be linked to the enzyme. Selective acylation of a glycerophosphocholine at the sn-1 position can be carried out by controlling the reaction temperature (0° C.) and the amount of the acylating agent. Furthermore, attachment of the sn-2 chain of the lipid to the substrate is preferable compared to the sn-1 chain since in the L-α-configuration of the lipid, the substrate-sn-2 chain linkage would leave both the sn-1 chain and the head group oriented away from the substrate surface, a condition favourable for enzyme binding and for effective functioning of the lipid in preserving the activity of the enzyme, in analogy with the orientation of natural biomembranes.

Figure 3:
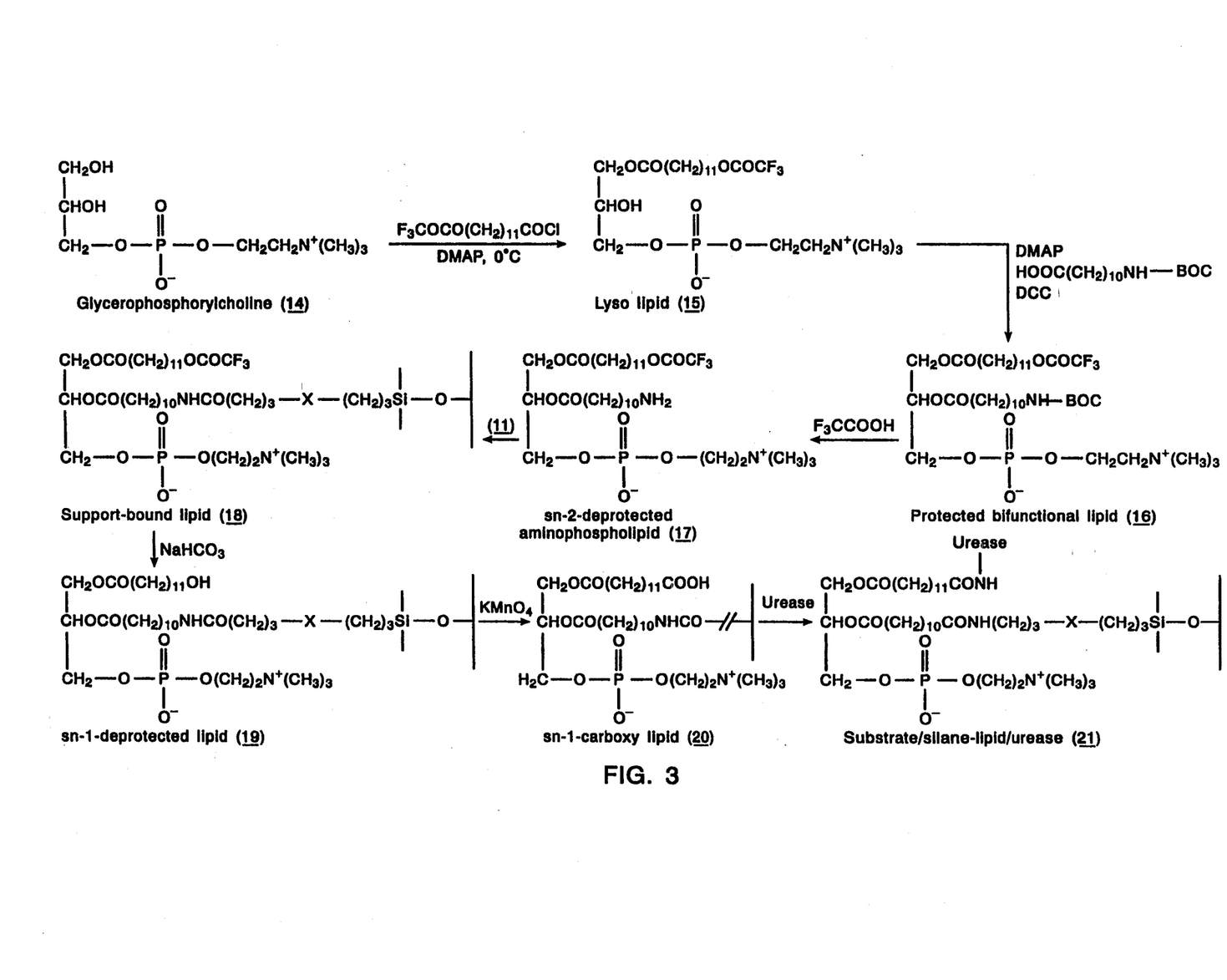
FIG. 3 illustrates the synthesis of bifunctional phospholipids and their coupling to support and to the enzyme.

FIG. 3 illustrates the eight-step synthetic sequence to effect the binding of the phosphocholine class of lipids to the substrate and to the enzyme. Condensation of glycerophosphorylcholine with 12-trifluoroacetoxydodecanoyl chloride at 0° C. yields the lyso lipid 15 which is further acylated with 11-t-butoxycarbonylamino undecanoic acid in the presence of a diimide to furnish the diacyl bifunctional lipid 16. Making use of the stability of the trifluoroacetyl protective group to mildly acidic reagents and the lability of the BOC group to the same, the latter is removed from 16 to generate the sn-2 terminal free amino group 17 (FIG. 3). This free amino group is bound to the surface carboxyl of either substrate 1 or 2 to form the phospholipid-bound substrate 18. In the next stage, deprotection of the trifluoroacetyl group on the sn-1 chain is carried out under mildly basic conditions and the liberated free hydroxyl 19 is oxidized to carboxyl 20 with neutral permanganate. The carboxyl was activated to its NHS-ester and coupled with urease in aqueous medium to give the silane-lipid-enzyme structure 21.

Figure 4:
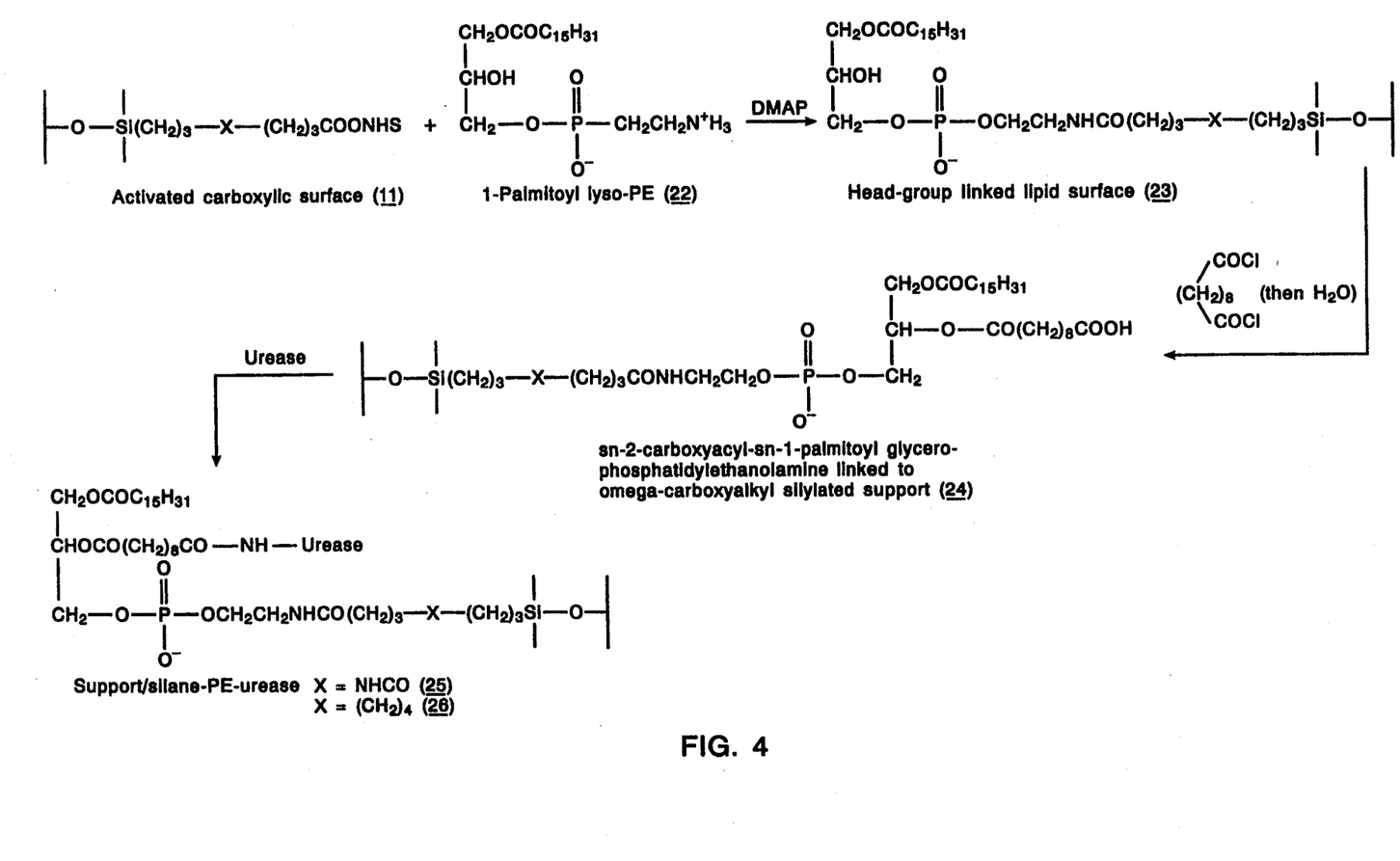
FIG. 4 illustrates the preparation and use of bifunctional phosphatidylethanolamines

In order to ascertain the effect of a surface lipid with a reverse configuration to that described above, a different strategy was developed to bind a phosphatidylethanolamine to the substrate through the head group and bind the enzyme to the sn-2 acyl chain. This protocol is illustrated in FIG. 4. It consists of initially binding 1-palmitoyl-sn-glycerophosphatidylethanolamine 22 to either of the NHS-activated surfaces 11 to furnish the head group-attached surfaces 23, which were subsequently treated with sebacoyl chloride to introduce the omega-carboxy functionality on the sn-2 chain (compound 24). These terminal carboxyls were activated with NHS and coupled with urease to furnish the silane-lipid-enzyme surfaces 25 and 26, respectively.

In this strategy, the amino moiety of the phosphatidylethanolamine is utilized as one of the two required functionalities and the second one is formed on the sn-2 chain. Therefore, a monofunctional phosphatidylethanolamine serves the same purpose as a bi-functional phosphocholine.

Spectrophotometric measurements

The results of the spectrometric measurements are presented in Table II. The data indicates that a C-11 spacer arm facilitates the immobilization of more urease than a C-6 arm (surfaces 2 and 1, respectively). The proportion of active enzyme is also larger with the longer spacer arm-carrying surface. However, the most striking feature is that the lipid-containing enzyme-linked surfaces exhibit a higher active enzyme content (10–20% more) compared to immobilized enzyme surfaces without the lipid and the proportion of the active enzyme remains more or less constant after 48 hours standing. Further, even if the substrates were heated in an oven to 100° C. for 15 minutes, they were found to still retain the same amount of active enzyme.

Change of pH from 4 to 8 also did not seem to have any significant effect on the activity of the lipid-bound enzyme, as observed by preliminary experiments within the scope of this invention.

The results obtained in this work clearly demonstrate that enzymes linked to silanized substrates through phospholipid intermediate cross-linkers retain almost their entire activity in the solid phase even after several days of storage. The covalent linkage of the phospholipids has been found to eliminate leakage problems associated with physisorbed phospholipids, experienced by earlier workers, and to provide a stable lipid-bound enzyme-based biosensory device. It can be concluded that phospholipids exert a stabilizing influence on immobilized enzymes to a considerable extent.

While the experiments conducted to validate the present invention were limited in the choice of substrates, spacer compounds, lipids and bioactive substances, it will be appreciated by those skilled in the art that the invention lends itself to a broader interpretation.

In particular, it is possible to use any solid substrate as defined hereinabove as long as the substrate features specific functional groups enabling the attachment of spacer compounds. While the functional groups tested herein were carboxylic and amino, it is feasible to utilize the other functional groups and adjust the functionality of the spacer compounds accordingly. For example, surface aldehyde functionalities, generated by the periodate oxidation of a polysaccharide support, could be coupled to an amino group on a long chain diamine used as a spacer. Analogously, an epoxy or a halo functionality introduced onto the surface of a synthetic polymer could be linked to an amino moiety on a diamine spacer.

With respect to spacer molecules, alkoxysilanes with long alkyl chains (7–18 carbons) carrying terminal carboxylic moieties can be successfully utilized for immobilizing bioactive substances on hydroxy-functionalized supports either directly or through phospholipids. Where non-hydroxylic polymeric materials are used as supports, other spacers like long chain diamines or dicarboxylic acids or omega-mercapto carboxylic acids can be made use of.

The main features in the invention, viz. phospholipid-stabilized biomolecules in the immobilized state, could be utilized for a variety of other purposes such as drug delivery systems, solid-state hormonal/steroidal formulations, enzyme-linked immunosorbent assays, contact lenses and other bioreactor applications.

TABLE I

X-RAY PHOTOELECTRON SPECTROSCOPIC DATA ON THE CAROXYLIC SURFACES 1 AND 2 AND ON SURFACES WITH LIPID AND/OR ENZYME BOUND TO THEM

| SURFACE STUDIED | ELEMENTAL COMPOSITION | | | | | HIGH RESOLUTION DATA | | | | | |
|---|---|---|---|---|---|---|---|---|---|---|---|
| | % C | % N | % P | % Si | % O | b.e. (eV) | area (%) | b.e. (eV) | area (%) | b.e. (Ev) | area (%) |
| 1 | 44.7 | 3.4 | — | 24.4 | 27.5 | 285.0 | 81.5 | 400.8 | 100.0 | 99.0 | 85 |
| | | | | | | 286.9 | 12.4 | | | 102.5 | 15 |
| | | | | | | 288.8 | 6.1 | | | | |
| 2 | 63.7 | — | — | 14.1 | 22.2 | 285.0 | 80.4 | — | — | 98.8 | 74 |
| | | | | | | 286.7 | 13.2 | | | 102.9 | 26 |
| | | | | | | 288.5 | 6.4 | | | | |
| 1 + Urease | 63.2 | 6.9 | — | 3.2 | 26.6 | 285.0 | 59.0 | 400.2 | 100.0 | 98.9 | 87 |
| | | | | | | 286.3 | 23.4 | | | 102.3 | 13 |
| | | | | | | 288.2 | 17.6 | | | | |
| 2 + Urease | 68.9 | 4.1 | — | 12.5 | 14.5 | 285.0 | 71.1 | 400.3 | 100.0 | 98.9 | 87 |
| | | | | | | 286.4 | 18.4 | | | 102.7 | 13 |
| | | | | | | 288.2 | 10.5 | | | | |
| 1 + Lipid | 79.7 | 2.1 | 1.1 | 2.2 | 14.9 | 285.0 | 72.1 | 400.0 | 61.0 | 99.2 | 60 |
| | | | | | | 286.2 | 11.8 | 402.2 | 39.0 | 101.5 | 40 |
| | | | | | | 287.0 | 8.2 | | | | |
| | | | | | | 289.3 | 7.7 | | | | |
| 2 + Lipid | 80.3 | 2.1 | 1.1 | 2.0 | 14.5 | 285.0 | 73.5 | 400.0 | 52.1 | 99.2 | 55 |
| | | | | | | 286.3 | 17.8 | 402.3 | 48.9 | 102.4 | 45 |

TABLE I-continued

X-RAY PHOTOELECTRON SPECTROSCOPIC DATA ON THE CAROXYLIC SURFACES 1 AND 2 AND ON SURFACES WITH LIPID AND/OR ENZYME BOUND TO THEM

| SURFACE STUDIED | ELEMENTAL COMPOSITION | | | | | HIGH RESOLUTION DATA | | | | | |
|---|---|---|---|---|---|---|---|---|---|---|---|
| | % C | % N | % P | % Si | % O | b.e. (eV) | area (%) | b.e. (eV) | area (%) | b.e. (Ev) | area (%) |
| 1 + Lipid + Urease | 71.1 | 6.7 | 1.8 | 4.6 | 15.8 | 287.1 | 4.6 | | | | |
| | | | | | | 288.8 | 4.2 | | | | |
| | | | | | | 285.0 | 78.1 | 400.1 | 71.0 | 99.0 | 69 |
| | | | | | | 286.3 | 10.9 | 402.2 | 29.0 | 101.4 | 31 |
| | | | | | | 287.1 | 4.2 | | | | |
| | | | | | | 288.1 | 6.9 | | | | |
| 2 + Lipid + Urease | 76.9 | 6.7 | 1.3 | 2.4 | 12.7 | 285.0 | 70.6 | 400.0 | 69.0 | 99.0 | 68 |
| | | | | | | 286.4 | 20.1 | 402.2 | 31.0 | 102.6 | 32 |
| | | | | | | 287.1 | 3.2 | | | | |
| | | | | | | 288.4 | 6.1 | | | | |

TABLE II

RESULTS OF SPECTROSCOPIC STUDIES

| Substrate treated with 1 mg Urease | Assay of Unbound Enzyme | | | Total immobilization yield (%) | Assay of Immobilzied active enzyme | | | | | |
|---|---|---|---|---|---|---|---|---|---|---|
| | | | | | After one hour | | | After 48 hours | | |
| | Absorption* | Amount (mg) | (%) | | Absorption* | Amount (mg) | (%) | Absorption | Amount (mg) | (%) |
| 1 | 0.99012 | 0.6 | 60 | 40 | 0.54122 | 0.268 | 67 | 0.55844# | 0.028 | 7 |
| 2 | 0.935100 | 0.55 | 55 | 45 | 0.65020 | 0.351 | 78 | 0.91578# | 0.054 | 12 |
| 1 + Lipid | 0.88746 | 0.52 | 52 | 48 | 0.76525 | 0.432 | 90 | 0.74133 | 0.413 | .86 |
| 2 + Lipid | 0.71686 | 0.40 | 40 | 60 | 0.91563 | 0.540 | 90 | 0.88708 | 0.516 | .86 |

*absorbance of solution diluted ten times
absorbance measured without dilution
Structure of Substrate 1: —O—Si(CH$_3$)$_2$(CH$_2$)$_3$NHCO(CH$_2$)$_3$COOH
Structure of Substrate 2: —O—Si(CH$_2$)$_{10}$COOH

We claim:

1. A preparation comprising
   a solid support
   a monolayer forming spacer compound having an alkyl chain containing 7–18 carbon atoms, said spacer compound covalently bound to said support,
   a monolayer forming bifunctional phospholipid with two dissimilar functional groups, said phospholipid covalently bound to said spacer compound with one of said functional groups, and
   a biologically active protein covalently bound to said phospholipid through the other functional group of the latter.

2. A preparation of claim 1 wherein the spacer compound is a non-polymerizable alkoxyalkylsilane with an alkyl chain containing 7 to 18 carbon atoms, including a terminal carbon atom, free of substituents on the alkyl chain, said alkoxyalkylsilane carrying an added function on the terminal carbon atom of said chain.

3. The preparation of claim 2 wherein the added function on the alkoxyalkylsilane is a carboxylic moiety.

4. The preparation of claim 1 wherein the spacer compound is an aliphatic dicarboxylic acid.

5. The preparation of claim 2 where the alkoxysilane is an omega-carboxyacylaminopropylalkoxysilane.

6. The preparation of claim 1 wherein the spacer compound is a diamine.

7. The preparation according to claim 1 wherein the biologically active protein is an enzyme.

8. A preparation of claim 1 wherein the solid support is selected from the group consisting of metals, metal oxide composites, silicon-based semiconductors, ceramics, and natural or synthetic polymers having, prior to the linkage with the spacer compound, hydroxyl groups or functional groups that can be converted into hydroxyls.

9. The preparation according to claim 1 wherein said biologically active substance is an antibody.

10. The preparation according to claim 1 wherein said biologically active substance is an antigen.

11. The preparation according to claim 1 wherein said phospholipid has two constituent sn chains and each of said functional groups is located at terminal carbon atoms of the two constituent sn chains.

12. A method of making a preparation comprising a biologically active protein immobilized on a solid support, the method comprising the steps of:
   a) providing a solid support with hydroxyl groups
   b) covalently linking to said support a monolayer-forming spacer compound having an alkyl chain containing 7–18 carbon atoms,
   c) covalently bonding to said spacer compound a monolayer-forming bifunctional phospholipid having two dissimilar functional groups through one of said functional groups, and
   d) covalently bonding to said bifunctional phospholipid a biologically active protein through the other functional group of said phospholipid.

13. The method of claim 12 wherein the biologically active protein is an enzyme.

14. The method of claim 12 wherein the spacer compound of step b) is an alkoxysilane having a straight alkyl chain with 7–18 carbon atoms and carrying a masked terminal carboxylic function that is capable of liberating the free carboxyl upon hydrolysis.

15. The method of claim 12 wherein the bifunctional phospholipid is a modified bifunctional phosphatidylcholine.

16. The method of claim 12 wherein the bifunctional phospholipid is a modified monofunctional phosphatidylethanolamine.

17. The method according to claim 12 wherein the spacer compound is linked to said support through a siloxane bond.

18. The method according to claim 12 comprising the step of forming in step b) a carboxyalkylsilyl structure of the spacer compound on said support.

19. The method according to claim 15 wherein the bifunctional phosphatidylcholine prior to its bonding to the spacer compound is prepared by the steps of:
a) providing a glycerophosphorylcholine having an sn-1 hydroxyl group
b) protecting the sn-1 hydroxyl group of the choline of step a),
c) treating the choline of step b) with omega-protected aminocarboxylic acid,
d) deprotecting the sn-1 protection of the choline of step c), and
e) introducing an omega-protected hydroxyacyl chain onto the sn-1 carbon by reacting the choline of step d) with omega-protected hydroxycarboxylic acid.

20. The method of claim 12 wherein the phospholipid before bonding to said spacer compound has protective moieties on said two functionalities, the method comprising the steps of selectively removing one of said protective moieties of the phospholipid for bonding with the spacer compound and subsequently removing the other protective moiety for bonding with the biologically active protein.

* * * * *